(12) United States Patent
Rutkowski et al.

(10) Patent No.: US 8,501,093 B2
(45) Date of Patent: Aug. 6, 2013

(54) PORTABLE HANDHELD MEDICAL DIAGNOSTIC DEVICES WITH COLOR-CHANGING INDICATIOR

(75) Inventors: Paul S. Rutkowski, Carmel, IN (US); Robert G. Davies, Carmel, IN (US); Mark Mears, Zionsville, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 115 days.

(21) Appl. No.: 12/482,688

(22) Filed: Jun. 11, 2009

(65) Prior Publication Data
US 2010/0317951 A1 Dec. 16, 2010

(51) Int. Cl.
*G01N 15/06* (2006.01)

(52) U.S. Cl.
USPC ........... 422/68.1; 422/52; 422/73; 422/82.01; 422/82.05; 422/82.06; 422/82.07; 422/82.08; 422/82.09; 422/82.11; 422/407; 422/501; 422/502; 422/503; 422/504; 422/507; 436/164; 436/177; 436/43; 436/63; 436/149; 436/172; 436/174; 436/518; 436/805; 436/809; 435/4; 435/29; 435/7.1; 506/30; 250/214.1; 250/251; 250/576; 530/408; 714/752

(58) Field of Classification Search
USPC ........... 422/68.1, 82.05, 52, 73, 82.01, 82.06, 422/82.07, 82.08, 82.09, 82.11, 407, 501, 422/502, 503, 504, 507; 436/164, 177, 43, 436/63, 149, 172, 174, 518, 805, 809; 435/29, 435/4, 6, 7.1; 506/30; 250/214.1, 251, 576; 530/408; 714/752
See application file for complete search history.

(56) References Cited

U.S. PATENT DOCUMENTS

| | | | |
|---|---|---|---|
| 5,636,044 | A | 6/1997 | Yuan et al. |
| 5,644,330 | A | 7/1997 | Catchpole et al. |
| 6,034,752 | A | 3/2000 | Khan et al. |
| 6,133,895 | A | 10/2000 | Huang |
| 6,172,720 | B1 | 1/2001 | Khan et al. |
| 6,268,840 | B1 | 7/2001 | Huang |
| 6,366,330 | B1 | 4/2002 | Khan et al. |
| 6,377,321 | B1 | 4/2002 | Khan et al. |
| 6,483,563 | B2 | 11/2002 | Khan et al. |
| 6,514,460 | B1 | 2/2003 | Fendrock |
| 6,518,944 | B1 | 2/2003 | Doane et al. |
| 6,532,052 | B1 | 3/2003 | Khan et al. |
| 6,654,080 | B1 | 11/2003 | Khan et al. |
| 6,830,789 | B2 | 12/2004 | Doane et al. |
| 6,911,965 | B2 | 6/2005 | Miller, IV |

(Continued)

FOREIGN PATENT DOCUMENTS
WO 2008078128 A1 7/2008

OTHER PUBLICATIONS

Celentano et al, U.S. Appl. No. 60/937,933, filed Jun. 29, 2007, p. 29 of Appendix.*

(Continued)

*Primary Examiner* — Dennis M White
(74) *Attorney, Agent, or Firm* — Dinsmore & Shohl LLP (57) ABSTRACT

A portable handheld medical diagnostic device includes a housing forming a protective enclosure. A main circuit board is located in the protective enclosure. The main circuit board includes a controller facilitating a physiologic measurement. A display device is connected to the main circuit board that displays information related to the physiologic measurement. An electronic skin is on the housing. The electronic skin comprises a liquid crystal material and is configured to display a color.

22 Claims, 9 Drawing Sheets

U.S. PATENT DOCUMENTS

| | | |
|---|---|---|
| 7,009,666 B2 | 3/2006 | Khan et al. |
| 7,023,409 B2 | 4/2006 | Blackson et al. |
| 7,061,559 B2 | 6/2006 | Khan et al. |
| 7,170,481 B2 | 1/2007 | Doane et al. |
| 7,190,337 B2 | 3/2007 | Miller, IV et al. |
| 7,236,151 B2 | 6/2007 | Doane et al. |
| 7,351,506 B2 | 4/2008 | Schneider et al. |
| 7,479,940 B2 | 1/2009 | Marhefka |
| 2002/0030776 A1 | 3/2002 | Khan et al. |
| 2002/0101554 A1 | 8/2002 | Khan et al. |
| 2002/0109661 A1 | 8/2002 | Blackson et al. |
| 2003/0231552 A1* | 12/2003 | Markart ............ 368/10 |
| 2004/0145548 A1 | 7/2004 | Miller |
| 2004/0171956 A1 | 9/2004 | Babashan |
| 2005/0063199 A1 | 3/2005 | Levy et al. |
| 2006/0103641 A1 | 5/2006 | Marhefka |
| 2006/0121625 A1* | 6/2006 | Clemens et al. .......... 436/514 |
| 2007/0093786 A1* | 4/2007 | Goldsmith et al. ........ 604/890.1 |
| 2007/0126674 A1 | 6/2007 | Doane et al. |
| 2007/0195031 A1 | 8/2007 | Miller et al. |
| 2007/0220427 A1* | 9/2007 | Briancon et al. ............ 715/700 |
| 2007/0237906 A1 | 10/2007 | Li et al. |
| 2007/0272564 A1* | 11/2007 | Huang ............ 205/792 |
| 2007/0279350 A1 | 12/2007 | Huang et al. |
| 2008/0037306 A1 | 2/2008 | Marhefka et al. |
| 2009/0033811 A1 | 2/2009 | Schneider |
| 2009/0051560 A1 | 2/2009 | Manning et al. |
| 2009/0096942 A1 | 4/2009 | Schneider et al. |
| 2010/0160759 A1* | 6/2010 | Celentano et al. ........... 600/365 |

OTHER PUBLICATIONS

International Search Report and Written Opinion of the EPO as ISA as it relates to PCT/EP2010/003485 mailed Oct. 13, 2010.

* cited by examiner

PORTABLE HANDHELD MEDICAL DIAGNOSTIC DEVICES WITH COLOR-CHANGING INDICATIOR

TECHNICAL FIELD

The present invention relates generally to portable, handheld medical devices, and in particular a portable, handheld medical diagnostic device including one or more color-changing indicators.

BACKGROUND

Portable handheld medical diagnostic devices are often employed to measure concentrations of biologically significant components of bodily fluids, such as, for example, glucose concentration in blood. The portable handheld medical diagnostic devices and their accessories may work together to measure the amount of glucose in blood and be used to monitor blood glucose in one's home, healthcare facility or other location, for example, by persons having diabetes or by a healthcare professional.

For people with diabetes, regular testing of blood glucose level can be an important part of diabetes management. Thus, it is desirable to provide medical diagnostic devices that are portable and easy to use. Various medical diagnostic devices have been introduced for testing blood sugar that are portable. However, there continues to be a need for improved portability and ease of use for medical diagnostic devices.

SUMMARY

In one embodiment, a portable handheld medical diagnostic device includes a housing forming a protective enclosure. A main circuit board is located in the protective enclosure. The main circuit board includes a controller facilitating a physiologic measurement. A display device is connected to the main circuit board that displays information related to the physiologic measurement. An electronic skin is on the housing. The electronic skin comprises a liquid crystal material and is configured to display a color.

In another embodiment, a method of indicating a physiologic measurement using a portable handheld medical diagnostic device is provided. The method includes (a) measuring a concentration of a biologically significant component of a bodily fluid using the portable handheld medical diagnostic device and (b) changing color of an electronic skin on the portable handheld medical diagnostic device based on the measuring step (a).

In still yet another embodiment, a portable handheld medical diagnostic device includes a housing forming a protective enclosure. A main circuit board is located in the protective enclosure. The main circuit board includes a controller facilitating a physiologic measurement. A display device is connected to the main circuit board that displays information related to the physiologic measurement. An electronic skin is on the housing. The electronic skin is configured to display a color. A strip port assembly is configured to receive a test strip for testing a blood sample. The strip port assembly comprises a strip port accessible from outside the protective enclosure for inserting a test strip. At least part of the strip port is formed of a material selected for distribution of light to illuminate the at least part of the strip port.

These and other advantages and features of the invention disclosed herein, will be made more apparent from the description, drawings and claims that follow.

BRIEF DESCRIPTION OF THE DRAWINGS

The following detailed description of the embodiments of the present invention can be best understood when read in conjunction with the following drawings, where like structure is indicated with like reference numerals, and in which.

DETAILED DESCRIPTION

The following description of the preferred embodiment is merely exemplary in nature and is in no way intended to limit the invention or its application or uses.

The process of monitoring one's own blood glucose with a glucose meter is often referred to as self-monitoring of blood glucose (SMBG). In some cases, a portable handheld glucose meter may be used in SMBG, which may be a relatively small, battery-operated device.

To test glucose with a glucose meter, a small sample of blood may be placed on a disposable test strip. The portable handheld glucose meter may include a strip port that receives the disposable test strip. The test strip may be coated with chemicals (glucose oxidase, dehydrogenase, or hexokinase) that combine with glucose in blood. The portable handheld glucose meter then measures concentration of glucose in the blood sample. The portable handheld glucose meter then displays the glucose concentration as a number (or glucose measurement value).

Figure 1:
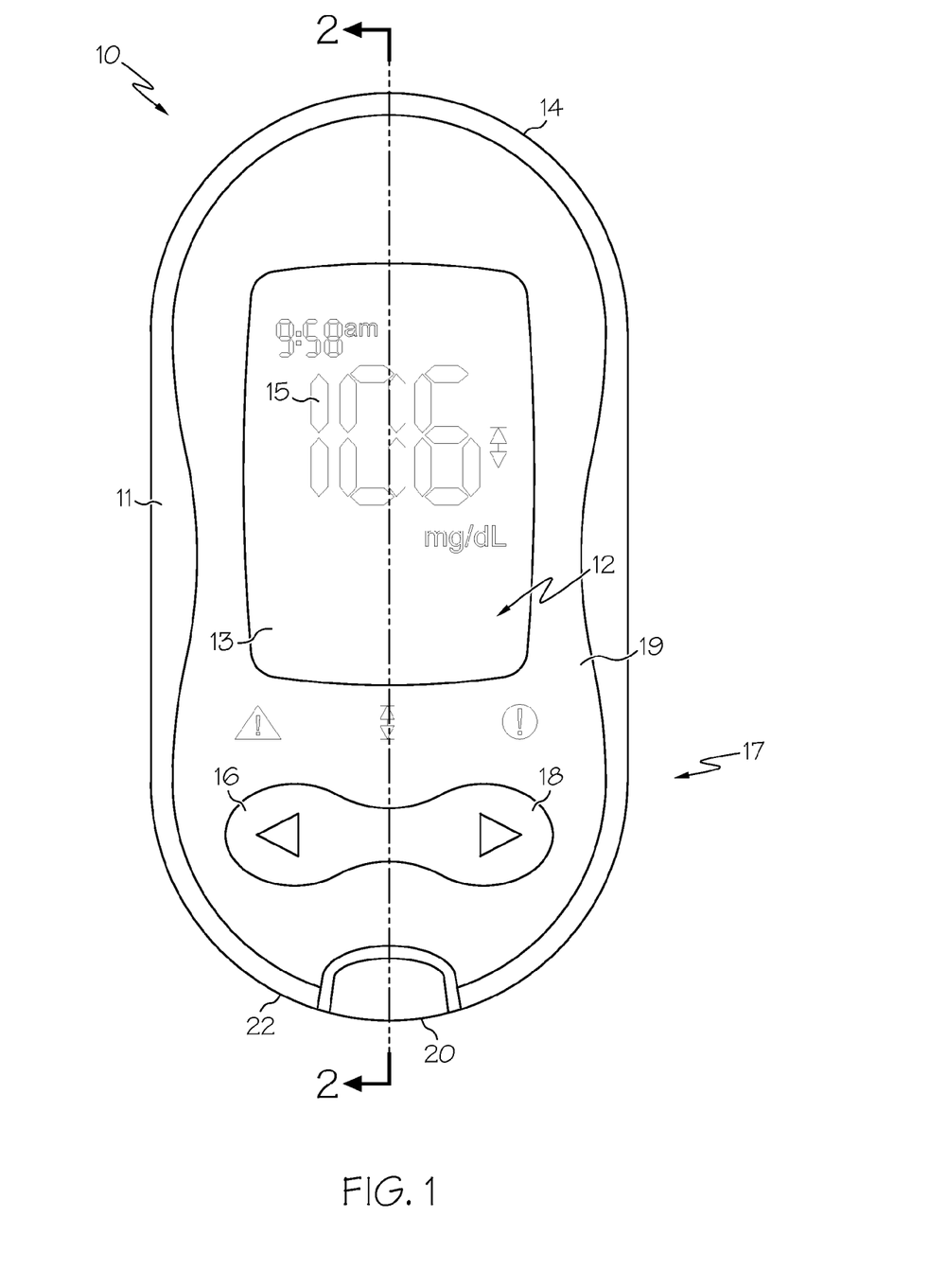
FIG. 1 is a front view of an embodiment of a medical diagnostic device.

Referring to FIG. 1, a portable, handheld medical diagnostic device 10 with a display device 12 behind a transparent, protective lens 13 includes a protective enclosure, generally indicated by symbol 14 that protects electronics therein. The protective enclosure 14 is somewhat oval in shape with an outer frame portion 11 and an hourglass-shaped inner portion 19 bounded by the frame portion. Any other suitable shapes may be used for the protective enclosure, frame portion 11 and inner portion 19, such as rectangular shapes, circular shapes, etc. The display device 12 may be any suitable display device used in a portable, handheld electronic device, such as, for example, but not limited to LCD display devices, LED display devices, OLED display devices, and other types of display devices which may be heretofore developed. Further, display device 12 may be any other variety of indicators, including, but not limited to a series of lights and/or other types of light devices as opposed to a single integrated display screen. In the illustrated embodiment, the display device 12 includes an electronic paper component such as an electrophoretic display, which may be an information display that forms visible images by rearranging charged pigment particles using an electric field. The display device 12 is used for electronically displaying graphics 15, text, and other elements to a user. In some embodiments, the display device 12 may be a touch-screen user interface that is used with the tip of a finger of the user and/or a stylus or other touching device to select elements from the screen, to draw figures, and to enter text with a character recognition program running on the device 10. In some embodiments, the medical diagnostic device 10 may also include other types of output devices such as for example, sound devices, vibration devices, etc.

The medical diagnostic device 10 further includes a user interface (generally referred to as element 17), which may include buttons 16 and 18. The buttons 16 and 18 are illustrated as right and left arrow buttons, but may be of any other suitable configuration. The buttons 16 and 18 may be used by an operator, for example, to view memory of the medical diagnostic device 10, adjust settings of the device and scroll through test results. The buttons 16 and 18 may be manually actuated, such as by pressing the buttons. In the illustrated embodiment, the buttons 16 and 18 comprise touch sensors (e.g., capacitive touch sensors) that can be actuated by placing a tip of the finger within the button areas. In this embodiment, the buttons 16 and 18 may not move. Instead, the buttons 16 and 18 may be indicated visually to identify where to place the finger. In other embodiments utilizing touch sensors, the buttons 16 and 18 may move, for example, to bring the finger or touching device into close proximity to the touch sensor. In some embodiments, the medical diagnostic device 10 may provide other button or input types such as an OK button and/or joy stick/track ball, which a user may utilize to navigate through a software drive menu provided on the display device 12. Additional buttons may be used as shortcut buttons, for example, to call up a certain program on the medical diagnostic device 10, as a method of scrolling, to select items from a list, or to provide any function that the software designer of the device may assign to the button or set of buttons. Each button size, layout, location, and function may vary for each manufacturer and model of the medical diagnostic device 10.

A test strip port 20 is located at a bottom 22 of the medical diagnostic device 10. The test strip port 20 is sized to receive a test strip for testing a blood sample. In one embodiment, the device 10 is an in vitro diagnostic device that is used to test blood and other body fluids and tissues to obtain information for the diagnosis, prevention and treatment of a disease. The medical diagnostic device 10 may be a self-testing blood glucose meter for people with diabetes. In one embodiment, the medical diagnostic device 10 is a handheld reagent-based blood glucose meter, which measures glucose concentration by observing some aspect of a chemical reaction between a reagent and the glucose in a fluid sample. The reagent may be a chemical compound that is known to react with glucose in a predictable manner, enabling the monitor to determine the concentration of glucose in the sample. For example, the medical diagnostic device 10 may be configured to measure a voltage or a current generated by the reaction between the glucose and the reagent.

A small test strip may be employed to hold the reagent and to host the reaction between the glucose and the reagent mentioned above. Accordingly, in one embodiment of the medical diagnostic device 10 as a blood glucose meter, the test strip port 20 is sized for inserting a test strip into the device 10. The test strip port 20 is used such that the reaction between the glucose and the reagent may be read electronically in order for the medical diagnostic device 10 to determine the concentration of glucose in the sample and display the results to a user. These embodiments enable both health care professionals and patients to perform reliable decentralized testing in hospitals, clinics, offices or patients' homes. In other embodiments, the medical diagnostic device 10 may form part of or include coagulation monitoring systems, professional blood glucose testing and monitoring systems, cardiac marker testing devices, blood gas/electrolyte testing, and urinalysis screening products. In some embodiments, environmental conditions may also be evaluated, for example, using a small AC signal.

Figure 2:
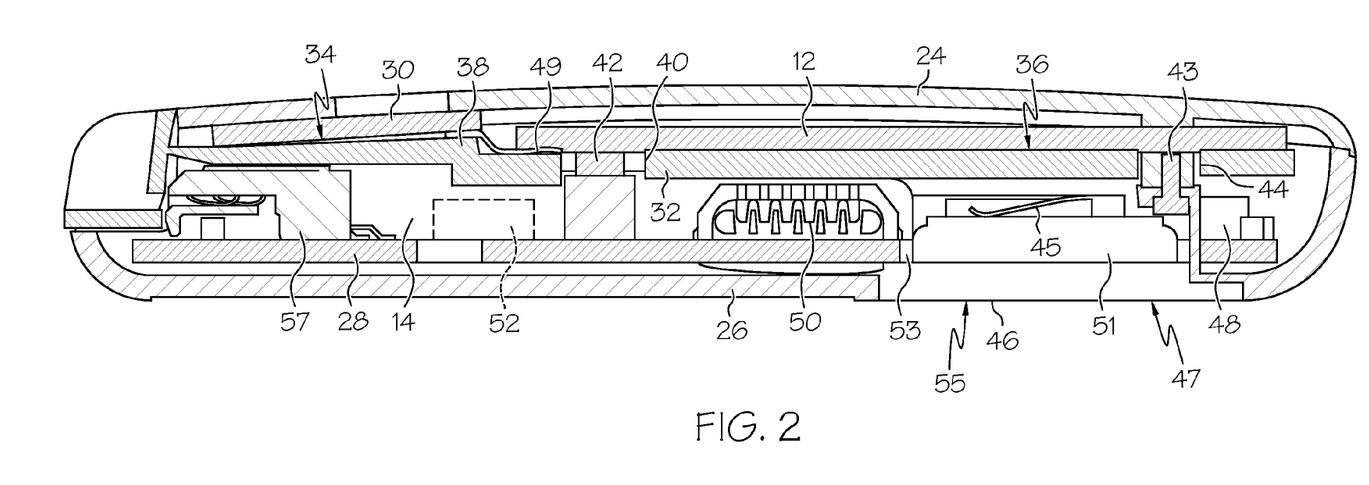
FIG. 2 is a diagrammatic section view of the medical diagnostic device along line 2-2 of FIG. 1.

Referring to FIG. 2, the protective enclosure 14 includes a front housing 24 and rear housing 26. As shown, the front and rear housings 24 and 26 mate to form a protective shell for internal components contained therein, such as for example, the display device 12, a main circuit board 28, and a touch sensor circuit board 30. The front housing 24 and the rear housing 26 may be formed from any of a variety of materials, including but not limited to polymeric materials, metals and metal alloys, combinations of metal and plastic materials, etc. In some embodiments, the front housing 24 and/or rear housing 26 may be formed using an in-mold decoration (IMD) process where a carrier foil that carries indicia is placed in the mold and transfers the indicia onto plastic forming the front and/or rear housing. The internal components of the medical diagnostic device 10 may be mounted in the protective enclosure 14 using any number of different mounting techniques. For example, in one embodiment, the internal components of the medical diagnostic device 10 may be mounted via open or closed cell foam inserts provided in the protective enclosure 14, or in another embodiment, they may be mounted via attaching the main circuit board 20 to an interior side of one of the front and rear housings 24 and 26 with a fastener. In another embodiment, the main circuit board may be mounted by a snap fit with an interior side of one of the front and rear housings 24 and 26.

In the embodiment illustrated by FIG. 2, the display device 12 and the touch sensor circuit board 30 are mounted within the protective enclosure 14 by a frame 32. The frame 32 may be formed from any of a variety of materials, including but not limited to polymeric materials, metals and metal alloys, combinations of plastic and metal materials, etc. The frame 32 includes a first board mounting section 34 and a second board mounting section 36. The first board mounting section 34 is shown as being elevated relative to the second board mounting section 36 with a step portion 38 located between the first and second board mounting sections. The first board mounting section 34 may be elevated to place the touch sensor circuit board 30 in close proximity to the front housing 24 and the buttons 16 and 18. Other configurations are possible, however, such as the first and second board mounting sections 34 and 36 being at about the same elevation or the second board mounting section being elevated relative to the first board mounting section. Additionally, there may be more or less than two board mounting portions. The frame 32 includes an opening 40 through which a board-to-board connector 42 extends, such as a 16 or 18 pin connector to connect the display device 12 to the main circuit board 28. The board-to-board connector 42 electrically connects the display device 12 to the main circuit board 28 in a stacked fashion, which situates the major surfaces of both the main circuit board 28 and the display device 12 in somewhat parallel planes within the protective enclosure 14. The frame 32 also includes a fastener opening 44 that receives a fastener 43 for connecting (e.g., threadably connecting) the front housing 24 and the rear housing 26. The fastener 43 can be accessed (e.g., for servicing of the medical diagnostic device 10) through a compartment 47. Other fastener openings and fastener locations may be provided. While the fastener 43 is shown, any suitable connection may be used to connect the front housing and the rear housing such as adhesives, welding, etc.

The touch sensor circuit board 30 is connected to the display device 12 using any suitable connector. In the illustrated embodiment, the touch sensor circuit board 30 is connected to the display device 12 using a flex cable connector 49. The flex cable connector 49 may be operatively attached to the touch sensor circuit board 30 and the display device 12 using, for example, a suitable hot bar soldering technique. The connection between the touch sensor circuit board 30 and the display device 12 allows for communication between the touch sensor circuit board 30 and the display device, for example, for control of the display device using information from the user interface 17 (FIG. 1).

Referring still to FIG. 2, a power supply 51 is provided within the compartment 47 of the protective enclosure 14 to provide power to the electrical/electronic components of the medical diagnostic device 10, for example, to allow use of the medical diagnostic device without a corded connection to an external power source. In some embodiments and as shown, the power supply 51 is a battery that is received through an opening 53 in the main circuit board 28 such that the battery is located at opposite sides of the main circuit board. Providing such an opening 53 allows the battery to nest with the main circuit board 28, which can reduce the thickness of the medical diagnostic device 10, for example, compared to a device which places the entire battery to only one side of a circuit board. Contacts (only negative contacts 45 are shown by FIG. 2) are provided to connect the power supply 51 to the electrical/electronic components of the medical diagnostic device 10. The power supply 51 is accessed and may be replaceable via a panel 46 provided in the rear housing 26, which provides and prevents access through opening 55 in the rear housing. The panel 46 may include any suitable attachment structure (e.g., a latch, fasteners, etc.) for releasably attaching the panel to the rear housing 26. In some embodiments, the panel 46 may be moveably connected to the rear housing 26 such as by a hinge or a sliding connection. In a rechargeable battery embodiment, the medical diagnostic device 10 may be sealed permanently with the original batteries installed by the manufacturer. In other words, the power supply 51 may not be replaceable. Additional power, such as for recharging the power supply 51, may be provided from a remote source of electricity that is transmitted to the medical diagnostic device 10 through a wire cable or through other methods of electrical transmission. For example, and in one embodiment, the medical diagnostic device 10 is rechargeable via a connected (wired) external device. It is to be appreciated that the medical diagnostic device 10 may provide a universal connection interface, which, in one embodiment, operates is a universal serial bus (USB) interface, and in another embodiment is a Firewire interface, and either of which provides a wired connector which connects to a charger for charging the device 10 via the connected external device.

The main circuit board 28, in one embodiment, provides a wireless connectivity component (generally referred to as element 48) which is used for calibration, configuration, and/or communicate with other devices such as, for example, another meter, an insulin pump, a printer, a router/modem, and/or a PC. In one embodiment, the wireless connectivity component 48 provides infrared communications. In such an embodiment, the medical diagnostic device 10 communicates with a PC running a compatible software package such as, for example, Roche Diagnostic's Accu-Chek Compass diabetes care software via an IrDA-serial port adapter. Such an embodiment permits a user to download data from the medical diagnostic device 10 via the IR based wireless connectivity component 48 and stores results to the PC. In other embodiments, the wireless connectivity component (or module) 48 may be a Bluetooth system, a ZigBee system, a Certified Wireless USB system, a Near Field Communication (NFC) system, an Active RFID system, a Wi-Fi system, and combinations thereof.

A code key interface 50 may also be provided which is used to provide calibration data to a controller (represented by dashed lines 52) via a code key chip and which is used in the measurement of a test strip and in the calculation used to compute the glucose level. A clocking element, such as for example, a 32 kHz crystal, may also be provided on the main circuit board 28 for sampling timing performed by the strip reader and by an integrated digitally controlled oscillator to generate a high-speed clock required for the controller 52 and the other provided peripherals requiring a clock.

A strip reader 57 is located at the test strip port 20. In one embodiment, the strip reader 57 is a programmable mixed signal microcontroller (e.g. Texas Instruments MSP 430) specifically configured (e.g., application specific integrated circuit (ASIC)) to sample and read a disposable test strip provided to the strip port 20. The strip port 20 is used to connect the test strip electrically to the strip reader 57, which reads the test strip electronically in any suitable manner and provides such input to the controller 52 for analysis.

The front housing 24 and the rear housing 26 provide the protective enclosure 14, which is shaped to accommodate therein the touch sensor circuit board 30, the main circuit board 28, the frame 32 and the power supply 51. However, the shape and dimensions of front and rear housings 24 and 26 of the protective enclosure 14 may vary for each manufacturer and model of the medical diagnostic device 10.

Figure 3:
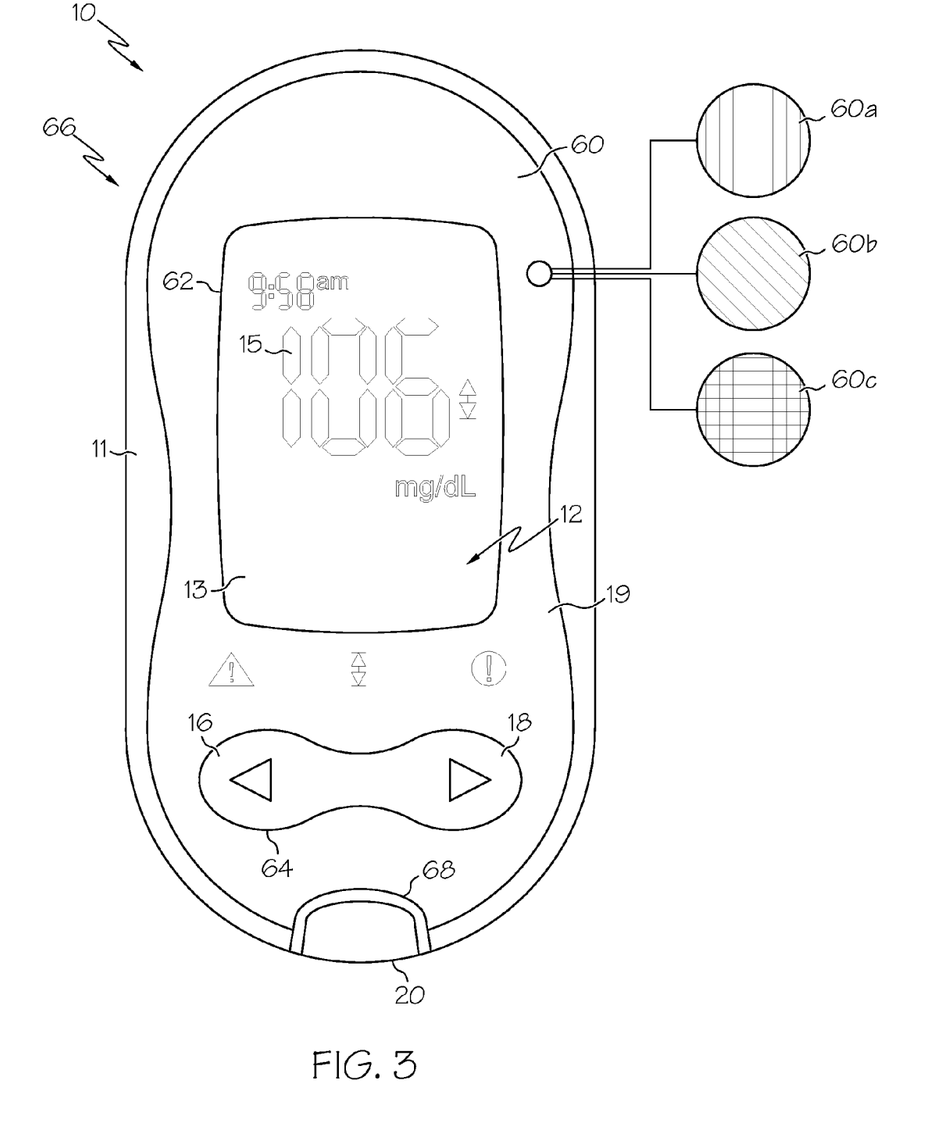
FIG. 3 is a front view of an embodiment of a medical diagnostic device including an embodiment of an electronic skin.

Referring to FIG. 3, the medical diagnostic device 10 may include one or more indicators that may be used to provide feedback to the user. In some embodiments, the medical diagnostic device 10 has a covering or skin 60, which is used to cover some or all of an outer surface area of the medical diagnostic device. In some embodiments, the skin 60 may include a first front opening 62 so that the display device 12 is exposed for viewing, a second front opening 64 so that the buttons 16 and 18 are exposed for finger placement, a side opening 66 so that the code key interface 50 is exposed and a bottom opening 68 so that the test strip port 20 is exposed. The skin 60 may be provided with more or less openings as needed for the particular medical diagnostic device to which it is applied.

The skin 60 may be flexible and applied to the medical diagnostic device 10 in any suitable manner. In one embodiment, the skin 60 may be removable from the medical diagnostic device 10 and may be sized to completely surround the medical diagnostic device with a protective barrier that can guard against minor dings, bumps and scrapes. In some embodiments, the skin 60 may include small plug protectors (e.g., rubber plugs that insert into the test strip port 20, the code key interface 50, etc. when not in use). The skin 60 may include a carrying strap and an attached microfiber screen clean. In some embodiments, the skin 60 may be permanently attached to the medical diagnostic device 10 (i.e., not removable without damaging the skin 60 and/or the medical diagnostic device). For example, the skin 60 may be adhered or otherwise attached to the medical diagnostic device 10. The skin 60 may be formed as a single piece of material or may be formed of multiple material pieces all of the same material or of different materials. Additionally, the skin 60 may include any number of connecting devices such as snaps, latches, tabs, etc.

In some embodiments, as shown, the skin 60 is an electronic skin capable of changing a visual indicator (e.g., colors, images, etc.) in response to an input. One exemplary electronic skin 60 may be a bistable display that uses polymer stabilized cholesteric liquid crystal (ChLCD) technology to generate the visual indicators. The term bistable means that there are two liquid crystal textures or states that remain after removal of an applied electric field. These two textures may be focal conic and planar, where the focal conic texture scatters impinging light and the planar texture reflects the impinging light. The skin 60 may be flexible and have the capability to be bent around edges of the medical diagnostic device 10. The skin 60 may be a color display or grayscale.

In the illustrated example, the skin 60 is a color display and the skin (the entire skin or portions thereof) may switch between, for example, red, green and yellow colors. Each of the colors may be used to indicate an event. For example, a red skin 60*a* may indicate a low bG level, a green skin 60*b* may be used to indicate a normal bG level and a yellow skin 60*c* may be used to indicate a high bG level. Additionally, colors may be user selected, for example, based on preference, mood, etc. instead of being automatically selected by the medical diagnostic device 10. In some embodiments, the user may choose what colors are associated with certain events and/or the medical diagnostic device 10 may be programmed to have certain colors associated with certain events. While three colors are illustrated, the skin 60 may be used to generate any number of colors. In some embodiments, the skin 60 may be capable of producing up to about 4500 different colors.

Figure 4:
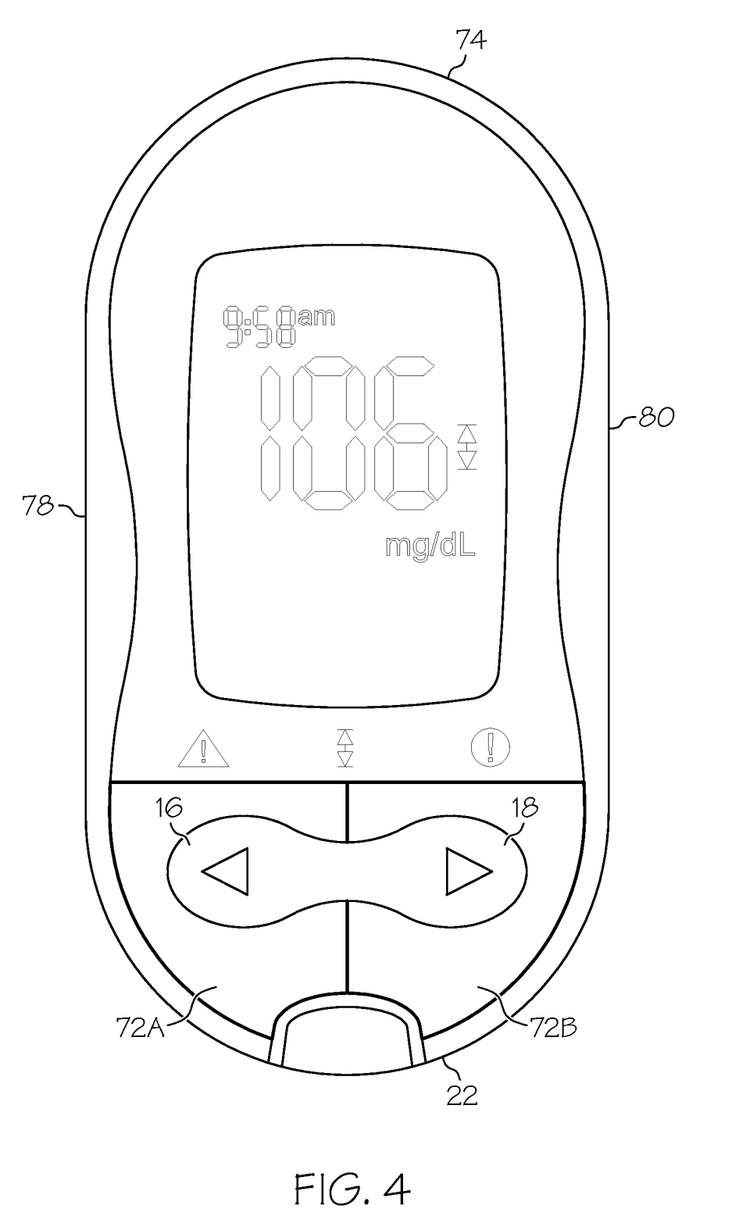
FIG. 4 is a front view of an embodiment of a medical diagnostic device including another embodiment of an electronic skin forming a multi-segment display.

Referring still to FIG. 3, the skin 60 is illustrated as being within inner portion 19 and bounded by the frame 11. In one embodiment, the skin 60 may extend continuously about the lens 70 and about the buttons 16 and 18, bounding the lens and the buttons. Referring briefly to FIG. 4, multiple electronic skin members 72A and 72B may be provided, for example, for a multi-segment display. The electronic skin may also extend all the way around the medical diagnostic device 10 and be bent around one or more of the top 74, bottom 22 and/or side edges 78 and 80. Additionally, the skin 60, and skin members 72A and 72B may change color or illuminate for multiple event types. For example, in FIG. 4, skin member 72A may illuminate when button 16 is actuated and skin member 72B may illuminate when button 18 is actuated. The skin members 72A and 72B may go dark when their associated buttons are released. Additionally, the skin members 72A and/or 72B may illuminate and/or change color in response to a different event, such as a bG reading, for example, without actuating buttons 16 and 18.

Figure 5:
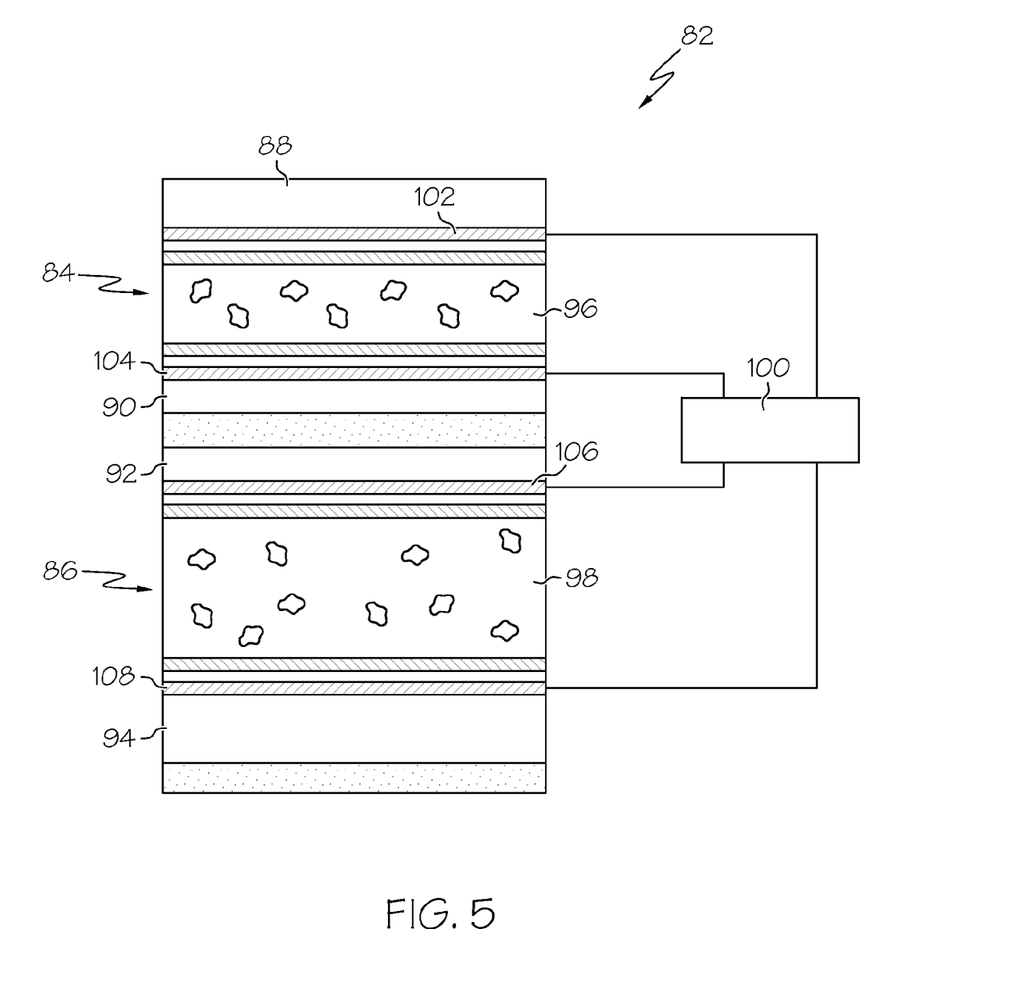
FIG. 5 is a diagrammatic, section view of an embodiment of a display forming an electronic skin.

Referring to FIG. 5, a simplified representation of the skin 60 includes the display shown generally at element 82. The display 82 includes two stacked cells 84 and 86 and four glass substrates 88, 90, 92 and 94. The cell 84 includes a first (chiral nematic) liquid crystal material 96 located between the opposing glass substrates 88 and 90 with the substrate 88 being located nearest an observer. The cell 86 on which the cell 84 is stacked includes a second chiral nematic liquid crystal material 98 located between the opposing glass substrates 92 and 94. While FIG. 5 illustrates two cells, more or less cells may be utilized.

In some embodiments, the first liquid crystal material 96 includes a concentration of chiral material that provides a pitch length effective to enable the material to reflect visible light at a first wavelength. The second liquid crystal material 98 may include a concentration of chiral material that provides a pitch length effective to enable the material to reflect visible light at a second wavelength different from the first wavelength.

The liquid crystal compositions may be designed to reflect light of any wavelength. For example, the first cell 84 may reflect red light, the second cell 86 may reflect blue light and a third cell (not shown) may reflect green light. In addition, to achieve a brighter stacked cell display, the liquid crystal in one cell may have a different twist sense than the liquid crystal of an adjacent cell for infrared/visible displays and color displays. For example, in a three cell stacked display, the top and bottom cells may have a right handed twist sense and the middle cell may have a left handed twist sense. Additional details for forming a color display are described in, for example, U.S. Pat. Nos. 6,377,321 and 7,351,506, the details of which are incorporated by reference in their entirety.

The back substrate of each cell may be painted a particular color or a separate color imparting layer may be used. Examples of color imparting layers are provided in U.S. Pat. No. 5,493,430, which is incorporated herein by reference in its entirety. The back substrate of the visible cell that is furthest from the observer may be painted black or a separate black layer may be used to improve contrast.

The bistable chiral nematic liquid crystal material may have either or both of the focal conic and twisted planar textures present in the cell in the absence of an electric field. In a pixel that is in the reflective planar state, incident light is reflected by the liquid crystal at a color determined by the selected pitch length of that cell. If a color layer or backplate is disposed at the back of that cell, light that is reflected by the pixel of that cell in the reflective planar state will be additive of the color of the liquid crystal and the color of the backplate. For example, a blue reflecting liquid crystal having an orange backplate will result in a generally white light reflected from the pixel in the reflective planar state. A pixel of the cell that is in the generally transparent focal conic state will reflect the orange color of the backplate to produce a white on orange, orange on white display. If a black layer is used at the back of the cell, rather than a colored backplate, the only color reflected will be that of the planar texture of the liquid crystal, since the black layer absorbs much of the other light. The color imparting layers of the visible cells and the black layer at the back substrate of the last visible cell are transparent so to enable light to travel to the next cell.

In the case of two or more cells, some incident light is reflected by the planar texture of the first cell at a particular color. Two or even three of the cells may be electrically addressed so as to have their liquid crystal transformed into the reflecting planar state, in which case the color reflected from the display would be produced by additive color mixing. Since not all of the incident light is reflected by the liquid crystal of the first cell, some light travels to the second cell where it is reflected by the planar texture of the second cell. Light that travels through the second cell is reflected by the planar texture of the third cell at a particular color. The color reflected by the first, second and third cells is additively mixed. The display 82 can reflect the colors of selected cells by only transforming the particular cell into the reflecting planar texture, the other cells being in the focal conic state. In this case, the resultant color may be monochrome.

Moreover, by utilizing grey scale by a process such as that disclosed in the U.S. Pat. No. 5,453,863, one or more cells of the display may be made to reflect light having any wavelength at various intensities. Thus, a full color display may be produced. The display may also be made to operate based upon principles of subtractive color mixing using a backlighting mode. The final color that is produced by various combinations of colors from each liquid crystal material, different colored backplates, and the use of grey scale, can be empirically addressed through observation. The entire cell may be addressed, or the cell may be patterned with electrodes to form an array of pixels, as would be appreciated by those skilled in the art in view of this disclosure.

A driver 100 may be used to drive the display 82. The driver 100 may be electrically coupled to electrode arrays 102, 104, 106 and 108, which allow the textures of the regions of display 82 to be individually controlled. Application of a voltage across the liquid crystal material can be used to adjust the texture of a picture element. Any suitable driver may be used to drive the display 82.

As noted above, the display 82 is used in forming the skin 60. In some embodiments, the display 82 may be formed on or integrally with a drapable substrate, such as a textile or fabric made of natural or man-made fibers or even non-fibrous materials such as polymeric sheets or films. The display 82 may also be drapable. The formability of a fabric or other drapable substrate material can be defined as its ability to re-form from a two-dimensional shape to a simple or complex three-dimensional shape. The drape coefficient is used to describe the degree of 3-D deformation when the fabric specimen is draped over a drapemeter as described, for example, in the publication: "Effect of Woven Fabric Anisotropy on Drape Behavior," ISSN 1392-1320, Materials Science (Medziagotyra), Vol. 9, No. 1, pp. 111 115 (2003) by V. Sidabraitre and V. Masteikaite, or "Modeling the Fused Panel for a Numerical Simulation of Drape" Fibers and Textiles, Vol. 12, pages 47-52 (2004), by S. Jevsnik and J. Gersak, incorporated herein by reference. Drapability is a phenomenon that occurs when a material such as a curtain, flag, table cloth or flared skirt hangs from an object. The drape coefficient, DC, describes any deformation between draped and undraped material. In terms of percentage, it is described by the ratio: $DC=100(S_P-\pi R_1^2)/(\pi R_2^2-\pi R_1^2)$ were $R_2$ is the radius of a circular cut of non-deformed fabric; $R_1$, the radius of a horizontal disc holding the fabric, and Sp the projected area of the draped specimen, including the part covered by the horizontal disc. The value of DC varies between zero and 100%. Since the value of DC can depend on the values selected for $R_1$ and $R_2$ of the drapemeter, $R_1$ may be selected to be 9 cm and $R_2$ may be selected to be 15 cm. The larger the value of the drape coefficient, the stiffer the fabric and more difficult to reform. Alternatively, the lower the value of DC, the easier to reform and adapt to shapes. Some examples of fabric substrate materials include silk, cotton, nylon, rayon, polyester, Kevlar, or similar materials made of fibrous material formed by woven and non-woven means having the deformability of cloth. The flexible substrate may be selected to provide protection for the medical diagnostic device 10. Forming a flexible liquid crystal display on a flexible substrate is described in U.S. Pat. No. 7,236,151, the details of which are incorporated by reference in their entirety.

It is also contemplated that the display 82 be formed on an elastic substrate (e.g., formed of elastic fibers). In some embodiments, a portion of the elastic substrate may be treated, for example, with a coating material to make that portion of the elastic substrate inelastic. The display 82 may be formed upon the inelastic portion of the substrate.

Figure 6:
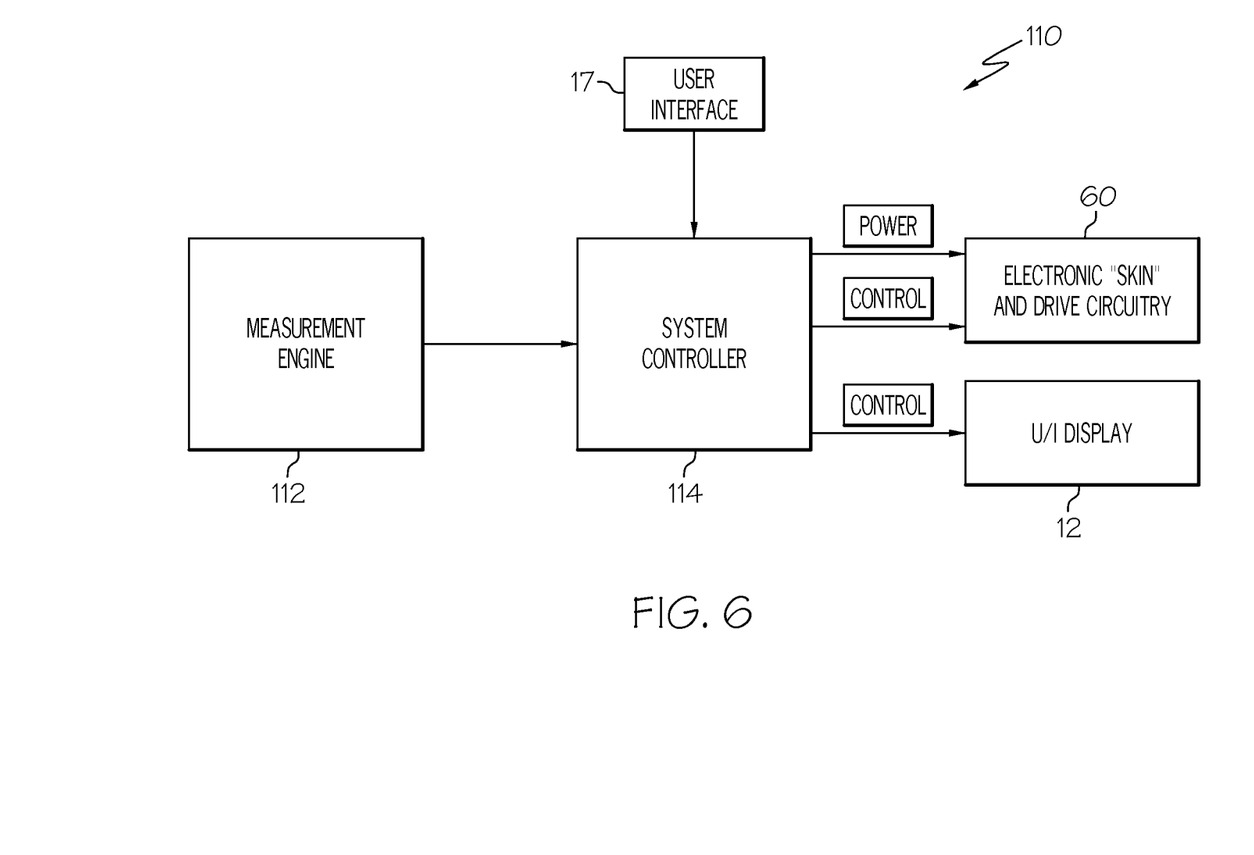
FIG. 6 is a diagrammatic illustration of an embodiment of a control system for controlling an electronic skin.

Referring to FIG. 6, an exemplary control system 110 for controlling the skin 60 (or skin members 72A and 72B) is shown. The control system 110 includes a measurement engine 112 that may read glucose and reagent on a test strip electronically to determine the concentration of glucose in the sample. The measurement data may be communicated to a system controller 114, which may process the measurement data to determine whether the measurement data falls within one or more predetermined glucose concentration ranges saved in memory. Based on this determination, the system controller 114 signals the driver to change color of the skin 60. The system controller 114 may also provide a signal (a voltage) capable of being used to drive the display. In some embodiments, the system controller 114 may also provide a control signal to the display device 12, for example, to display the measurement data and provide an indication of the range (e.g., low, normal, high, etc.). The user interface 17 may also provide input to the system controller 114 for selection of colors for the electronic skin 60. In some embodiments, the measurement engine 112 and system controller 114 may be part of controller 52 (FIG. 2).

Figure 7:
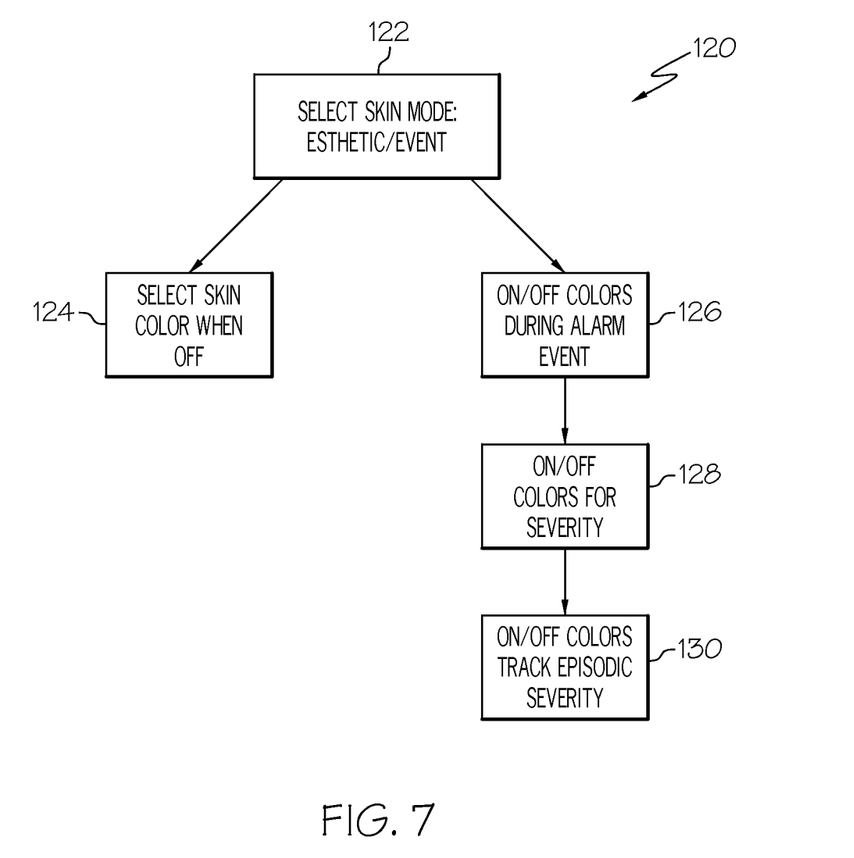
FIG. 7 is a diagrammatic illustration of an embodiment of a process for selecting a skin color for display.

Referring to FIG. 7, an exemplary process 120 is shown for selecting skin color. In some embodiments, the medical diagnostic device 10 may have one or more modes, such as an aesthetic mode and an event mode. At step 122, the operator chooses between the aesthetic mode and the event mode (e.g., using the user interface 17). In the aesthetic mode, a skin color may be chosen by the operator (or preprogrammed) and displayed at step 124 without regard to any events. As another embodiment, the skin may display a first color when the medical diagnostic device is ON and a second, different color when the medical diagnostic device is OFF. In the event mode, a skin color is displayed depending on an event. At step 126, a color may be displayed based on an alarm event. For example, a predetermined color may be displayed (or changed) at a preselected time, for example, at a time when a test sample should be provided to the medical diagnostic device 10. As another example, a predetermined color may be displayed (or changed) if the medical diagnostic device 10 has not received a test sample after a preselected time period. At step 128, a color may be displayed (or changed) based on severity of the test result. For example, one color (e.g., green) may be displayed if the test result falls within a normal range, another color (e.g., yellow) may be displayed if the test result is higher than the normal range and another color (e.g., red) may be displayed if the test result is lower than the normal range. In some embodiments, the tint of the color (e.g., green, yellow, red) may vary depending on where within the normal, high and low range the test measurement falls. At step 130, a color may be displayed (or change) to track episodic severity. For example, if a test result is low and a color (e.g., red) is displayed, the skin 60 may remain the same color until a test result is provided outside the low range. Other events may display other skin colors. For example, looking at test history may cause the skin 60 to display (or change) color.

Other skin color changing events may be used. For example, the skin 60 may illuminate or change color to indicate that a test strip has been fully inserted in the test strip port 20 and/or that the test strip is removed from the test strip port. The skin 60 may illuminate or change color when data is being transferred, for example, from the medical diagnostic device 10 to another device such as a computer. In some embodiments, the skin 60 may illuminate or change color to indicate whether or not a test trip is fully dosed.

Figure 8:
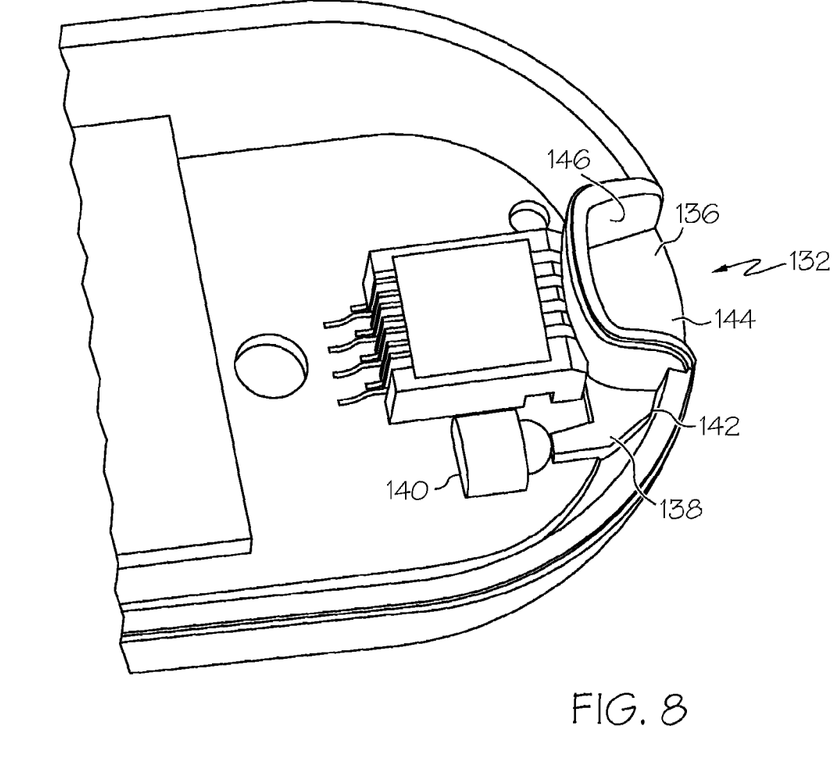
FIG. 8 is a diagrammatic perspective top view of an embodiment of an illuminated strip port assembly.

Referring to FIG. 8, the above described medical diagnostic device 10, in some embodiments, may include an illuminated strip port assembly 132. The illuminated strip port assembly 132 includes a strip port 136, a light pipe 138 and a light source 140 (e.g., an LED). A light pipe 138 is a tube or pipe for transport of light from one location to another location while minimizing the loss of light. The light pipe 138 may be formed of any suitable material, such as glass, plastic or a pipe with a highly reflective lining. The light pipe 138 transmits light from the light source 140 to the strip port 136

(or a portion thereof). The strip port 136 may be formed of a material selected for distribution of light over its length, either for equidistribution along the entire length or for controlled light leakage. The strip port 136 may be formed of any suitable material such as glass, plastic, etc. In the illustrated embodiment, the light pipe 138 may be formed of molded plastic with one or more prismatic turns 142 so that light reflects off the turns and does not travel straight into the strip port 136. In one embodiment, only a bottom shelf 144 of the strip port 136 may illuminate (e.g., the bottom shelf may be formed separately and/or of a different material than the rest of the strip port such as vertical wall 146). In another embodiment, the entire strip port 136 may illuminate. In some embodiments, the LED may be capable of providing a number of different colors for illuminating the strip port 136 using different color lighting. The different colors may provide different indications to a user. In some embodiments, the lighting is selected to illuminate the strip port 136 to allow a user to use the medical diagnostic device 10.

Figure 9:
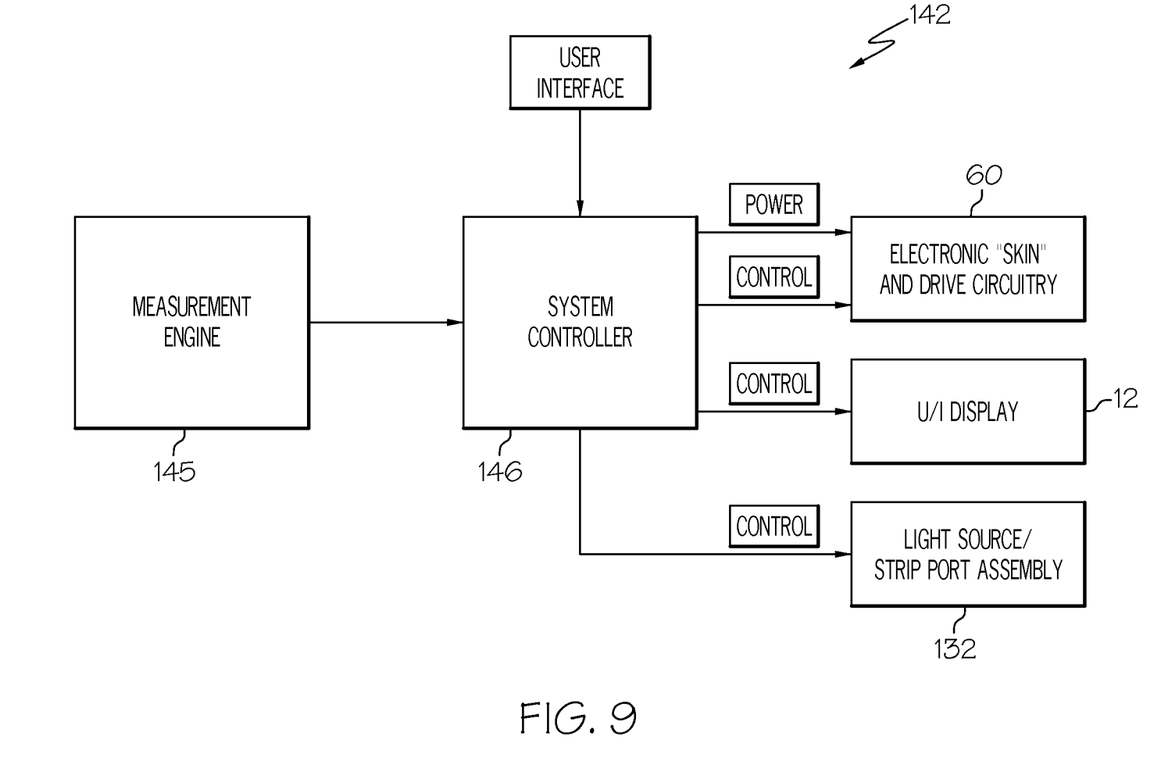
FIG. 9 is a diagrammatic illustration of an embodiment of a control system for controlling the illuminated strip port assembly and electronic skin.

Referring to FIG. 9, an exemplary control system 142 for controlling the skin 60 and illuminated strip port assembly 132 includes a measurement engine 145 that may read glucose and reagent on a test strip electronically to determine the concentration of glucose in the sample. The measurement data may be communicated to a system controller 146, which may process the measurement data to determine whether the measurement data falls within one or more predetermined glucose concentration ranges saved in memory. Based on this determination, the system controller 146 signals the driver to change color of the skin 60. The system controller 146 may also provide a signal (a voltage) capable of being used to drive the display. In some embodiments, the system controller 146 may also provide a control signal to the display device 12, for example, to display the measurement data and provide an indication of the range (e.g., low, normal, high, etc.).

The system controller 146 may also control the light source 140 such as ON/OFF and color of the light source. In some embodiments, the system controller 146 may coordinate operation and color of the light source 140 with operation of the skin 60. For example, the system controller 146 may operate the light source 140 such that the light source 140 is the same or a similar color as the skin 60. As another example, the system controller 146 may cause the light source 140 to be a different color than the skin, for example, to accentuate a position of the strip port 136. The user interface 17 may also provide input to the system controller 114 for selection of colors for the electronic skin 60 and the light source 140. In some embodiments, the measurement engine 112 and system controller 114 may be part of controller 52 (FIG. 2).

The above description and drawings are only to be considered illustrative of exemplary embodiments, which achieve the features and advantages of the present invention. Modification and substitutions to specific process steps, system, and setup can be made without departing from the spirit and scope of the present invention. For example, while the skin 60 may be used with a portable continuous glucose monitoring device. The skin 60 may illuminate or change color based on an alert level or alert condition. Accordingly, the invention is not to be considered as being limited by the foregoing description and drawings, but is only limited by the scope of the appended claims.

What is claimed is:

1. A portable handheld medical diagnostic device for a user, comprising:
   a housing forming a protective enclosure;
   a main circuit board located in the protective enclosure, the main circuit board including a controller which is configured to facilitate a physiological measurement;
   a single-piece frame located in the protective enclosure, the frame having a strip port formed therein;
   a display device mounted on the frame and connected to the main circuit board, wherein the display device is flat and rigid and displays information related to the physiological measurement; and
   an electronic skin on the housing separate from the display device, wherein the electronic skin is a color display and comprises a liquid crystal material, and is configured to display a color, wherein the controller is operatively connected to both the electronic skin and the display device, wherein the controller is configured to control the color of the electronic skin and configured to control the display of the information on the display device related to the physiological measurement, and wherein the controller is configured to permit selection by the user of the color of the electronic skin from a plurality of colors.

2. The portable handheld medical diagnostic device of claim 1, wherein the controller is configured to change the color of the electronic skin to a second, different color in response to the physiological measurement.

3. The portable handheld medical diagnostic device of claim 1, wherein the controller is configured to change the color of the electronic skin a second, different color based on a measurement value determined by the physiological measurement.

4. The portable handheld medical diagnostic device of claim 3, wherein the measurement value is a blood glucose concentration value.

5. The portable handheld medical diagnostic device of claim 4, wherein the controller is configured to change the electronic skin to the second, different color when the blood glucose concentration value is within a predetermined range of blood glucose concentration values.

6. The portable handheld medical diagnostic device of claim 1 further comprising a strip port assembly configured to receive a test strip for testing a blood sample.

7. The portable handheld medical diagnostic device of claim 6, wherein the strip port assembly comprises a strip port accessible from outside the protective enclosure for inserting a test strip, at least part of the strip port being formed of a material selected for distribution of light to illuminate the at least part of the strip port.

8. The portable handheld medical diagnostic device of claim 7, further comprising a light source used to illuminate the at least part of the strip port, and wherein the controller is configured to control the light source and is configured to permit selection by the user of a color illuminated by the light source.

9. The portable handheld medical diagnostic device of claim 7 further comprising:
   a light source remote from the strip port; and
   a light delivery device configured to transport light from the light source to the strip port.

10. A method of indicating a physiological measurement comprising:
    providing a medical diagnostic device which comprises a housing forming a protective enclosure, a main circuit board located in the protective enclosure, the main circuit board including a controller which is configured to facilitate a physiological measurement, a single-piece frame located in the protective enclosure, the frame having a strip port formed therein, a display device mounted on the frame and connected to the main circuit board, wherein the display device is flat and rigid and displays information related to the physiological measurement, and an electronic skin on the housing, wherein the electronic skin comprises a liquid crystal material and is configured to display a color, wherein the controller is operatively connected to both the electronic skin and the display device, wherein the controller is configured to control the color of the electronic skin and configured to control the display of the information on the display device related to the physiological measurement, and wherein the controller is configured to permit selection by the user of the color of the electronic skin from a plurality of colors;

receiving input on the medical diagnostic device which selects a first color of the electronic skin from the plurality of colors;

measuring a concentration of a biologically significant component of a bodily fluid using the portable handheld medical diagnostic device; and changing the first color of the electronic skin on the portable handheld medical diagnostic device automatically to a second, different color based on the measuring of the concentration of the biologically significant component of the bodily fluid.

11. The method of claim 10, further comprising changing the electronic skin automatically to the second, different color at a preselected time for the measuring of the concentration of the biologically significant component of the bodily fluid.

12. The method of claim 10, further comprising changing the electronic skin automatically to the second, different color if the device has not received the bodily fluid for measuring after a preselected time period.

13. The method of claim 10, wherein blood glucose concentration is the concentration of the biologically significant component of the bodily fluid, and said method further comprises changing the electronic skin automatically to the second, different color when a value of the blood glucose concentration is within a predetermined range of blood glucose concentration values.

14. The method of claim 10, further comprising changing the electronic skin automatically to the second, different color based on a result of the measuring of the concentration of the biologically significant component of the bodily fluid.

15. The method of claim 10 further comprising illuminating at least part of a strip port, the at least part of the strip port being formed of a material selected for distribution of light.

16. A portable handheld medical diagnostic device for use by a user, comprising:

a housing forming a protective enclosure;

a main circuit board located in the protective enclosure, the main circuit board including a controller which is configured to facilitate a physiological measurement via a measurement engine;

a light source;

a single-piece frame located in the protective enclosure, the frame having a strip port formed therein, wherein the strip port is accessible from outside of the protective enclosure, and at least part of the strip port is formed of a material selected for distribution of light from the light source to illuminate the at least part of the strip port with a first color;

a display device mounted on the frame and connected to the main circuit board, wherein the display device is flat and rigid and displays information related to the physiological measurement; and an electronic skin on the housing and separate from the display device, wherein the electronic skin provides an opening such that the display device is visible through the opening, and wherein the electronic skin is configured to display a first color; and wherein the controller is operatively connected to the electronic skin, the display device and the light source, the controller is configured to control displaying of the first and second colors, is configured to control the display of the information related to the physiological measurement on the display device, and is configured to permit selection by the user of both the first and second colors from a plurality of colors.

17. The portable handheld medical diagnostic device of claim 16, wherein the controller is configured to change the first color of the electronic skin automatically to another, different color in response to the physiological measurement.

18. The portable handheld medical diagnostic device of claim 16, wherein the controller is configured to change the first color of the electronic skin automatically to another, different color based on a result of the physiological measurement.

19. The portable handheld medical diagnostic device of claim 16, wherein the controller is configured to display both the first color of the electronic skin and the second color of the light source as the same color.

20. The portable handheld medical diagnostic device of claim 16, wherein the controller is configured to display the first color of the electronic skin automatically when the device is on and to change automatically the first color to another, different color when the device is turned off.

21. The portable handheld medical diagnostic device of claim 16, wherein the controller is configured to display the first color of the electronic skin automatically when the device is in an aesthetic mode and to change automatically the first color to another, different color when the device is in an event mode, wherein the event mode occurs upon at least one of insertion of the test strip into the strip port, removal of the test strip from the strip port, a result determined by the measurement engine, an alarm event, selecting of particular information to display on the display, transferring of data, and fully dosing the test strip with the blood sample.

22. The portable handheld medical diagnostic device of claim 16, wherein the controller is configured to display the second color of the light source as a different color from the first color of the electronic skin to accentuate position of the strip port on the device.

* * * * *

UNITED STATES PATENT AND TRADEMARK OFFICE
CERTIFICATE OF CORRECTION

PATENT NO. : 8,501,093 B2  
APPLICATION NO. : 12/482688  
DATED : August 6, 2013  
INVENTOR(S) : Rutkowski et al.

Page 1 of 1

It is certified that error appears in the above-identified patent and that said Letters Patent is hereby corrected as shown below:

On the title page, Item [54] and in the Specification, Column 1, Title

"PORTABLE HANDHELD MEDICAL DIAGNOSTIC DEVICES WITH COLOR-CHANGING INDICATIOR"

should read

--PORTABLE HANDHELD MEDICAL DIAGNOSTIC DEVICES WITH COLOR-CHANGING INDICATOR--

Signed and Sealed this  
Third Day of June, 2014

Michelle K. Lee  
*Deputy Director of the United States Patent and Trademark Office*